US00PP11567P

United States Patent [19]

Boeder

[11] Patent Number: Plant 11,567

[45] Date of Patent: Oct. 17, 2000

[54] CHRYSANTHEMUM PLANT NAMED 'KISKADEE'

[75] Inventor: Mark Boeder, West Wittering, United Kingdom

[73] Assignee: Cleangro Limited, United Kingdom

[21] Appl. No.: 09/167,019

[22] Filed: Oct. 6, 1998

[51] Int. Cl.[7] ..... A01H 5/00

[52] U.S. Cl. ..... Plt./295

[58] Field of Search ..... Plt./295

*Primary Examiner*—Howard J. Locker
*Attorney, Agent, or Firm*—Christie, Parker & Hale, LLP

[57] ABSTRACT

A new plant variety of chrysanthemum producing yellow daisy-type flowers.

1 Drawing Sheet

BACKGROUND OF THE INVENTION

The present invention is directed to a new and distinct variety of *Chrysanthemum morifolium*. The varietal denomination of the new chrysanthemum is 'Kiskadee'.

The female parent of the new variety is the variety known as 'Vera' and the male parent is an undistributed variety identified as G63-C7. The new variety has been asexually reproduced by vegetative cuttings in Ventura County, Calif. and the distinguishing characteristics are retained through successive generations of asexual reproduction.

SUMMARY OF THE INVENTION

'Kiskadee' produces yellow daisy-type flowers of different coloration then its parents on a green mounding plant.

COMPARISON WITH PARENT

Parent variety 'Vera' has ray florets of different color and smaller flowers than the new variety.

BRIEF DESCRIPTION OF ILLUSTRATION

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. in the month of July. 'Kiskadee' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that of the life of individual blooms of 'Kiskadee' is about 25 days and the response time is about 6.5 weeks. No growth retardant was used on plants described. Useful growing conditions include night temperatures of about 62°–68° F. and day temperatures of about 65°–70° F. at about 5000 foot candles light. The natural season response in Ventura County, Calif. is early September, depending upon climate and plant conditions.

Plant: Herbaceous perennial garden plant.

*Habit*.—Mounding.

*Height*.—About 23 cm.

*Number of breaks from pinch*.—About 3.

*Length of lateral branches*.—About 17 cm.

*Stem color*.—Near 138A.

*Stem surface*.—Lightly pubescent.

Foliage:

*Leaf arrangement*.—Alternate.

*Number of leaves per lateral branch*.—About 15 fully expanded leaves.

*Leaf size*.—Length: About 5.4 cm. Width: About 3.3 cm.

*Leaf shape*.—Ovate.

*Attachment*.—Petioled.

*Leaf apex*.—Obtuse.

*Base*.—Tapered.

*Margin*.—Palmately lobed, few serrations.

*Aspect*.—Slightly undulate.

*Surface*.—Top: slightly pubescent. Bottom. slightly pubescent.

*Venation color*.—Upper surface: Near 137D. Under surface: Near 137C.

*Petiole*.—Length: About 1 cm. Color: Near 137D.

*Color*.—Mature leaf: Top: Near 137A. Bottom: Near 137C. Young leaf: Top: Near 137A. Bottom: Near 137D.

Flower:

*Inflorescence form*.—Cyme.

*Bloom type*.—Daisy.

*Number of blooms per branch*.—About 9.

*Diameter of fully expanded bloom*.—About 5 cm.

*Depth of fully expanded bloom*.—About 1.5 cm.

*Sepal number*.—About 18 . Color: Near 137B.

*Peduncle*.—Length: Penduncle length is shortest at the terminal flower and progressively longer moving down the stem, the longest peduncle length is on average about 6 cm, the shortest peduncle length is on average about 3.3 cm. Aspect: Straight. Surface: Pubescent. Color: Near 138A. Disc diameter: About 2 cm.

*Flower Bud* (*when just showing color*).—Color: Near 13C. Diameter: Near 0.9 cm. Height: About 1 cm.

*Ray florets*.—Number per flower: About 36. Texture: Matte. Shape: Oblanceolate. Apex: Obtuse. Margin: Entire. Aspect: Slightly undulate. Length: About 2.5 cm. Width: About 0.7 cm.

*Disc florets*.—Number per flower: About 125. Texture: Shiny. Shape: Cylindric. Length: About 0.5 cm.

*Fragrance*.—Faint, musky.

Flower color:

*General flower description*.—Bright yellow daisy with a yellow/orange center.

*Ray florets, top side*.—Immature: Near 13B. Mature: Near 14B. Fading: Near 14C.

*Ray florets, under side*.—Immature: Near 7B. Mature: Near 7A. Fading: Near 7D.

*Disc florets*.—Immature: Near 151C. Mature: Near 14B. Fading: Near 15B.

*Changes as the flower ages*.—Ray florets become more loosely held. Considerable pollen is released by the disc florets.

Reproductive organs:

*Ray florets*.—Pistillate. Stigma shape: 2 branched. Stigma color: Near 7A. Style length: About 0.4 cm. Style color: Near 154D.

*Disc florets*.—Stigma shape: 2 branched. Stigma color: Near 17B. Style Length: About 0.6 cm. Style color: Near 4D. Stamen number: About 5. Anther length: About 0.4 cm. Pollen color: Near 14A. Pollen quantity: Abundant.

What is claimed is:

1. A new and distinct chrysanthemum plant of the variety substantially as herein shown and described.

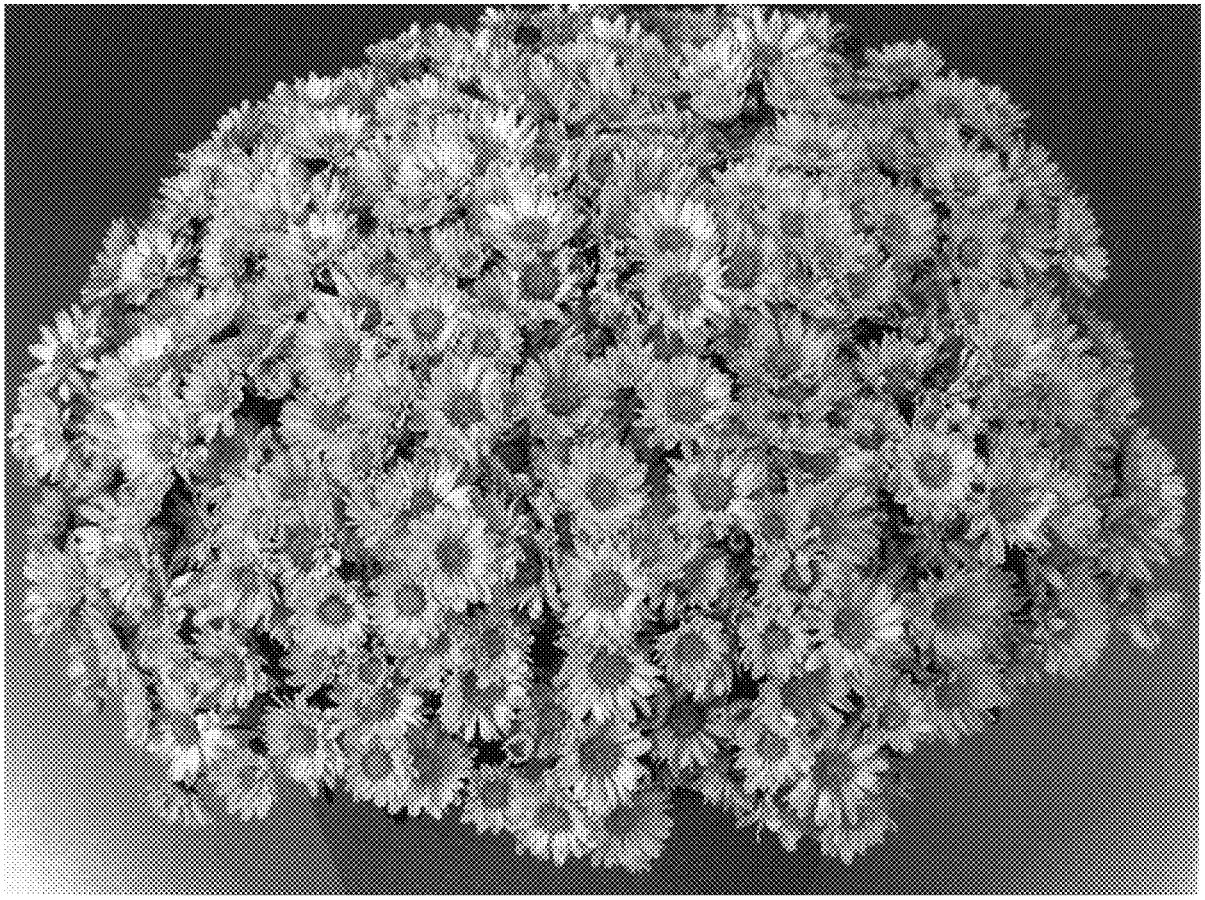

* * * * *